United States Patent [19]

Mosbach et al.

[11] Patent Number: 4,962,099

[45] Date of Patent: Oct. 9, 1990

[54] CHEMICAL SYNTHESIS

[75] Inventors: Erwin H. Mosbach; Charles K. McSherry, both of New York, N.Y.; Mizuho Une, Hiroshima, Japan; Naoyuki Matoba, New York, N.Y.

[73] Assignee: Beth Israel Medical Center, New York, N.Y.

[21] Appl. No.: 293,327

[22] Filed: Jan. 5, 1989

Related U.S. Application Data

[63] Continuation-in-part of Ser. No. 141,828, Jan. 11, 1988, abandoned.

[51] Int. Cl.$^5$ ............................................. A61K 31/56
[52] U.S. Cl. ..................................... 514/177; 552/551
[58] Field of Search ............................... 514/177, 552; 260/397.1

[56] References Cited

U.S. PATENT DOCUMENTS 4,545,938  10/1985  Mosbach et al. ................... 552/551
4,648,995   3/1987  Mosbach et al. ................. 260/397.1

OTHER PUBLICATIONS

Chemical Abstracts, vol. 89:209225j (1978).
Chemical Abstracts, vol. 94:95469n (1981).

*Primary Examiner*—Douglas W. Robinson
*Assistant Examiner*—Kevin E. Weddington

[57] ABSTRACT

A process for the production of disubstituted bile acid analogs, including the disubstituted analogs of such bile acids as, lithocholic, hyodeoxycholic, cholic, chenodeoxycholic and ursodeoxycholic acids.

This invention was made in the course of work performed under a grant from the U.S. National Heart Lung and Blood Institute.

8 Claims, No Drawings

CHEMICAL SYNTHESIS

This application is a continuation in part application of copending prior filed application Ser. No. 141828 filed Jan. 11, 1988.

This invention relates to and has as its objectives the provision of various useful compounds by means of new processes for their production. More particularly, this invention relates to physiologically active steroidal compounds and to novel processes for their production.

The final physiologically active compounds of this invention are compounds of the formulae:

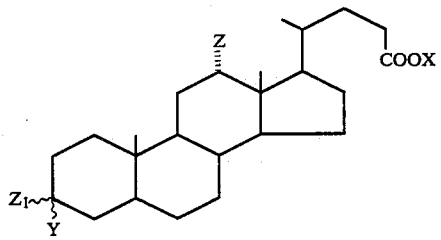

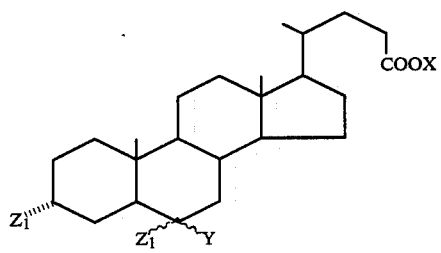

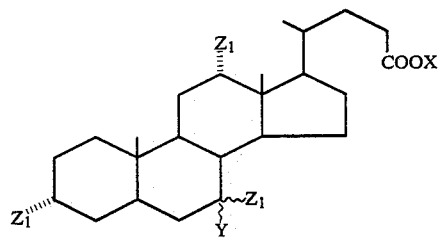

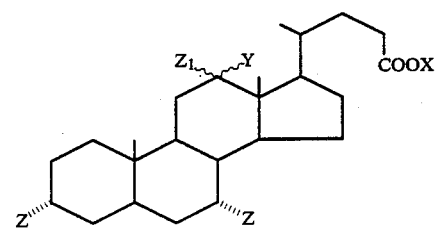

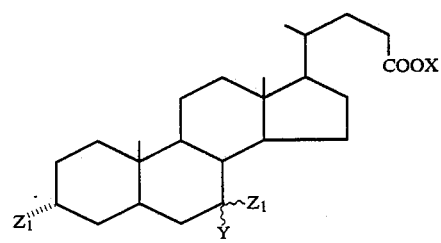

wherein R may be H or acyl; X may be H, acyl or lower alkyl; Z may be H, hydroxy or acyloxy; $Z_1$ may be hydroxy or acyloxy; Y is alkyl; and the non-toxic pharmaceutically acceptable salts thereof. In its preferred embodiment, the practice of this invention provides compounds of the above formulae, wherein R is H or acyl; X is H, acyl or methyl; Z is H, hydroxy or acyloxy; $Z_1$ is hydroxy or acyloxy; Y is methyl; and in its most preferred embodiment, this invention provides compounds of the above formulae, wherein R is H; X is H or acyl; Z is hydroxy or acyloxy; $Z_1$ is hydroxy or acyloxy; Y is methyl; and the non-toxic, pharmaceutically acceptable salts thereof, although the other final compounds of this invention also provide satisfactory results.

The final compounds of this invention are physiologically active compounds and may be employed in various therapeutic treatments in the same manner and to the same extent as disclosed for their bile acid analogs, for example, the disubstituted derivatives of chenodeoxycholic and ursodeoxycholic acid may be employed in the same manner and same purposes as taught in U.S. Pat. No. 3,859,437 issued Jan. 8, 1975. The amounts and periods of administration of the compounds of the instant invention to the patient being treated therewith is within the purview of the knowledge of the skilled worker and will depend on the condition of the patient being treated and the result desired.

In order to obtain the satisfactory results from the instant invention, it will be necessary to administer the compounds of the instant invention to the patient being treated by a systemic route, for example, perorally, or parenterally. The compositions employed for such purposes should contain the compounds of this invention in a suitable systemically administerable, Pharmaceutically acceptable composition, all as is well known to the skilled worker. Thus, suitable injectable compositions, orally administerable pills, capsules or elixirs or other suitable, pharmaceutically acceptable compositions containing the active compounds of this invention may be employed in the practice thereof. The skilled worker is well equipped to determine the most suitable compositions and dosage forms to be employed in the practice of the instant invention.

The acyl moieties which may be employed in the practice of this invention include those acyl groups which are derived from hydrocarbon carboxylic acids of eighteen carbon atoms or less and include such acids as the alkanoic, cycloalkanoic, monocyclic acyl and monocyclic aralkyl acids.

Whenever in the specification hereof and the claims appended thereto in any structural formula contained therein a curved line ( $\xi$ ) is employed in the linkage of atoms, it is meant to denote that the substituent moiety may be, stereochemically, in either the α or β position, depending upon the compound involved. The alkly substituents of the compounds of this invention may be alkyl moieties having from one to twelve carbon atoms and in its preferable embodiment, the compounds of this invention may contain lower alkyl substituents having from one to six carbon atoms, while in its most preferable embodiment, the alkyl moieties of this invention are methyl or ethyl substituents.

Heretofore, the final compounds of this invention were prepared by a process which required a multitude of separate reaction steps. This prior art process which is set forth in U.S. Pat. No. 4,545,938, while providing certain of the final products of this invention has an overall yield of less than 10%. In addition, it has been found not to be chemically possible to produce some of the final products of this invention by the prior art processes. Hence, these prior art processes are not only not commercially feasible, especially in view of the relatively large amounts of final product required for the therapeutic treatment of patients; they are also not chemically feasible in that they do not permit the production of many of the compounds of the instant invention.

The final compounds of this invention may be prepared in accordance with the processes of this invention employing as starting material a keto cholanoate compound selected from the group consisting of compounds of the formulae:

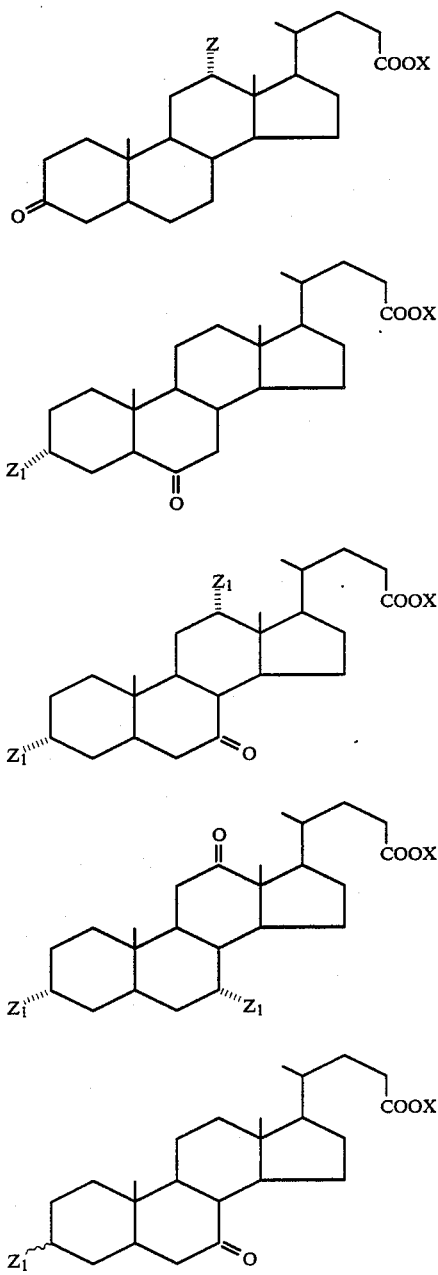

wherein $Z_1$ and X are as previously defined. Included among those keto choloanoic acid starting materials which may be employed in the practice of this invention are such compounds as, 3-keto-lithocholic acid; 6-keto-hyodeoxycholic acid; 12-keto-cholic acid; 7-keto-cholic acid; 7-keto-chenodeoxycholic acid; 7-keto-ursodeoxycholic acid; 12-keto-deoxycholic acid; 3-keto-deoxycholic acid and other known keto cholanoic acids. The starting materials may then be treated with a reactant having the following formula: Y-W-(Hal), under mild reaction conditions, to directly yield the final corresponding disubstituted compounds of this invention. Many of the disubstituted final products of this invention are new and novel compounds.

In general, the reactants which may be employed in the practice of this invention have the formula, Y-W-(Hal), wherein Y is as hereinabove defined; W is selected from the group consisting of magnesium and manganese; and Hal is a halide selected from the group consisting of Br, Cl, I and F. Although satisfactory results are obtained with a large number of the reactants employable herein, in its most preferred embodiment, this invention provides the most satisfactory results where Y is alkyl of twelve carbon atoms or less; W is Mg; and Hal is I, Br, or Cl. Most preferably, Y is lower alkyl; W is Mg; and Hal is I, Cl or Br. The skilled worker may select the reactant most suitable for the practice of the instant process.

The process of the instant invention must be conducted under mild reaction conditions. The mild reaction conditions employed require that the temperature of reaction be maintained at 40C. or below and at one atmosphere pressure or less. Most preferably, the reaction should be conducted at ambient temperature and pressure. The worker skilled in the art will, of course, be cognizant of the mild reaction conditions required for the practice of the instant invention.

The instant invention may be illustrated by the following examples:

EXAMPLE I 3α,
7α-dihydroxy-7β-methyl-5β-cholanoic acid

Methyl magnesium iodide (30mmol) was added to a solution of methyl 3α-hydroxy-7-oxo-5β-cholanoate (4.04 g, 10 mmol) in 100 ml of dry ether and stirring was continued at room temperature for 2 hours. At the end of this period, the reaction mixture was poured into 200 ml of water, acidified with 1N HCl, and extracted twice with 200 ml of ether. The combined ether extracts were washed with water, dried over Na₂SO₄, and the solvent was removed in vacuo.

The residue (4 g) was chromatographed on a silica gel column (100 g) using increasing proportions of ethyl acetate in benzene after methylation with diazomethane. Elution of the column with benzene-ethyl acetate, 7:3, v/v, resulted in the recovery of 848 mg of the starting material. Further elution with benzene-ethyl acetate, 6:4 and 4:6, v/v, afforded methyl 3α, 7α-dihydroxy-7β-methyl-5β-cholanoate. Alkaline hydrolysis of the methyl ester with 5% methanolic KOH (under reflux for 1 hour) gave 2.03g of 3α, 7α-dihydroxy-7β-methyl-5β-choloanoic acid. m.p. 96–99° C. (from methanol-water), PMR (δ ppm): 0.70(3H, s, 18—CH₃), 1.31(3H, s, 7,β-CH₃), 3.86(1H, m, 3 β-H).

In addition, minor amounts of 3α, 7β-dihydroxy-7α-methyl-5β-cholanoic acid were also obtained.

EXAMPLE II

3α,7α-Dihydroxy-7β-ethyl-5,β-cholanoic acid

Following the procedure of Example I but substituting an equivalent amount of ethyl magnesium bromide for methyl magnesium iodide, 3α,7β-dihydroxy-7β-ethyl-5β-cholanoic acid was obtained: PMR (δ ppm), 0.72(3H, s, 18—CH$_3$), 0.91(3H, s, 19—CH$_3$), 0.95(3H, t, J=6 Hz, —CH$_2$—CH$_3$), 0.99(3H, d, J=6 Hz, 21—CH$_3$), 3.73(1H, m, 3β—H).

EXAMPLE III

3α,7α-dihydroxy-7β-propyl-5β-cholanoic acid

Following the procedure of Example I but substituting an equivalent amount of n-propyl magnesium bromide for methyl magnesium iodide, there was obtained, 3α,7α-dihydroxy-7β-propyl-5β-cholanoic acid: PMR (δ ppm): 0.71(3H, s, 18—CH$_3$), 0.90(3H, s, 19—CH$_3$), 0.93(3H, t, J=Hz, 7—CH$_2$CH$_2$CH$_3$), 0.97 (3H, d, J=6Hz, 21—CH$_3$), 3.69(1H, m, 3β—H).

EXAMPLE IV

The procedure of Example I may be followed by equivalent amounts of tetrahydrofuran may be substituted for the ether with the same results being obtained.

EXAMPLE V

3α6α-dihydroxy-6β-methyl-5β-cholanoic acid and
3α,6β-dihydroxy-6α-methyl-5β-cholanoic acid 6 g. of methyl 3β-hydroxy-6-oxo-5β-cholanoate, obtained in accordance with Hoehn et al, 68 JACS 1855-7 (1946), were dissolved in 300 ml of tetrahydrofuran and 30 ml of a 3.0 M ethereal solution of methyl magnesium iodide were added. After stirring for 1 minute at room temperature, the reaction mixture was rapidly poured into 700 ml of acidified ice-cooled water and extracted twice with 500 ml of ether. The organic layer was washed with water, 10% Na$_2$S$_2$O$_3$, 5% NaHCO$_3$, and water until neutral. After drying over anhydrous Na$_2$SO$_4$, the solvents were evaporated in vacuo. The extracts were dissolved in 50 ml of 7% methanolic KOH and refluxed for 2 hours. Following dilution with 10 volumes of water, the neutral compounds were removed by extraction with ether. The acidic compounds were extracted with ethyl acetate after careful acidification with 1 N HCl to pH 2. The organic layer was washed with water until neutral, dried over anhydrous Na$_2$SO$_4$, filtered and evaporated in vacuo. Treatment with freshly prepared diazomethane gave an oily residue of bile acid methyl esters which was chromatographed on a 200 g. silica gel column using increasing Proportions of acetone in benzene. Fifteen percent acetone in benzene eluted 850 mg. of 3α,6α-dihydroxy-6β-methyl-5β-cholanoic acid as methyl ester; 3α,6β-dihydroxy-6α-methyl-5β-cholanoic acid was further eluted with 30% acetone in benzene. Alkaline hydrolysis of the two isomers with 7% methanolic KOH, followed by the foregoing standard extraction procedures afforded the corresponding free acids: 3α,6α-dihydroxy-6β-methyl-5,β-cholanoic acid, 710 mg, as a white solid from ethyl acetate: m.p. 135°-138° C; PMR 0.64 (3H, s, 18—CH$_3$), 0.92 (3H, d J=6Hz, 21—CH$_3$), 1.32 (3H, s, 19—CH$_3$), 1.42 (3H, s, 6α—CH$_3$), 3.50—3.98 (1H, m, 3β13 H); 3α,6β-dihydroxy-6α-methyl-5β-cholanoic acid, as white crystals from ethyl acetate, 490 mg, mp 186.5-188.0° C., PMR 0.65 (3H, s, 18—CH$_3$), 0.83 (3H, d, J=6Hz, 21—CH$_3$), 1.02 (3H, s, 19—CH$_3$), 1.65 (3H, s, 6α—CH$_3$), 3.70-4.10 (1H, m, 3β—H).

EXAMPLE VI

Following the procedure of Example V but substituting equivalent amounts of methyl magnesium bromide and methyl magnesium chloride for methyl magnesium iodide, like results were obtained.

EXAMPLE VII

Following the procedure in Example V but substituting equivalent amounts of ethyl magnesium iodide and propyl magnesium iodide for methyl magnesium iodide, the respective 6-ethyl and 6-propyl analogues of the final compounds of this invention were obtained.

EXAMPLE VIII

Following the procedure of Example V but substituting an equivalent amount of methyl manganese iodide for methyl magnesium iodide, like results were obtained.

EXAMPLE IX

Following the procedure of Example I, but substituting an equivalent amount of methyl 3α,12α-dihydroxy-7-oxo-5β-choloanate or methyl 3α, 7α-dihydroxy-12-oxo-5β-cholanoate for methyl 3α-hydroxy-7-oxo-5β-cholanoate there is obtained, respectively, 3α, 7α,12α-trihydroxy-7,β-methyl-5β-cholanoic acid and 3α,7α,12α-trihydroxy-12β-methyl-5β-cholanoic acid.

EXAMPLE X

Following the procedure of Example I but substituting an equivalent amount of methyl-3-oxo-5β-cholanoate for methyl. 3α-hydroxy-b 7-oxo-5β-cholanoate, there is obtained 3α-hYdroxy-3β-methyl-5β-cholanoic acid.

EXAMPLE XI

Various bile acids and bile acid analogues (0.05% of the diet) were incorporated into a semipurified, lithogenic diet (LD) and administered to groups of young male hamsters for 8 weeks. As a control, one group of animals was fed a semi-purified non-lithogenic diet. At the end of the experimental period, the animals were killed and the gallbladders were examined for the presence of gallstones and cholesterol crystals. The results obtained are set forth in Table 1 below. Chenodeoxycholic and ursodeoxycholic acid significantly lowered the incidence of cholesterol gallstones and biliary cholesterol crystals, as expected. However, with all 6-disubstituted bile acids of this invention, it was unexpectedly discovered that the formation of cholesterol gallstones was completely prevented.

TABLE 1

| | PREVENTION OF CHOLESTEROL GALLSTONES IN THE HAMSTER | | | |
|---|---|---|---|---|
| | | | INCIDENCE OF | |
| GROUP | DIET | NO. OF ANIMALS | CHOLESTEROL GALLSTONES | BILIARY CHOLESTEROL CRYSTALS |
| 1 | SPD | 20 | 0/20 | 0/20 |
| 2 | LD | 44 | 24/44 (54.5%) | 29/44 (65.9%) |

TABLE 1-continued

| | | | INCIDENCE OF | |
|---|---|---|---|---|
| GROUP | DIET | NO. OF ANIMALS | CHOLESTEROL GALLSTONES | BILIARY CHOLESTEROL CRYSTALS |
| 3 | LD + CDCA | 20 | 4/20** (30%) | 7/20 (35%) |
| 4 | LD + UDCA | 20 | 5/20** (25%) | 6/20 (30%) |
| 5 | LD + 6β-Me—HDCA | 11 | 0/11* (0%) | 2/11 (18%) |
| 6 | LD + 6αMe—MDCA | 9 | 0/9* (0%) | 0/9 (9%) |

*Differs from LD, P 0.005.
**Differs from LD, P 0.03.
SPD = Semipurfied, Non-Lithogenic Diet (0% Cholesterol).
LD = Lithogenic Diet = SPD + 0.3% Cholesterol.
CDCA = Chenodeoxycholic Acid
UDCA = Ursodeoxycholic Acid
6β-Me—HDCA = 3α,6α-Dihydroxy-6β-Methyl-5β-Cholanoic Acid.
6α-Me—MDCA = 3α,6β-Dihydroxy-6α-Methyl-5β-Cholanoic Acid.

The foregoing data demonstrate that the final compounds of this invention proces improved anti-cholelithiasis activity more potent than that of either chenodeoxycholic acid or ursodeoxycholic acid.

This invention may be further included within the ambit of the appended claims.

What is claimed is:

1. The compounds of the formula:

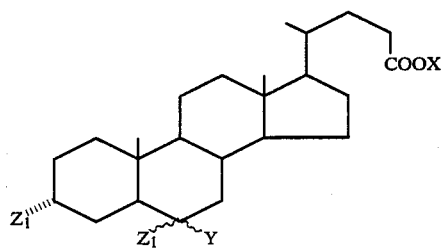

wherein each $Z_1$ may be OH or acyloxy; Y is alkyl; X may be H, acyl or lower alkyl; and the non-toxic pharmaceutically acceptable salts thereof.

2. The method of treating gallstones which comprses administering to the patient in need thereof a small but therapeutically effective amount of compound of the formula:

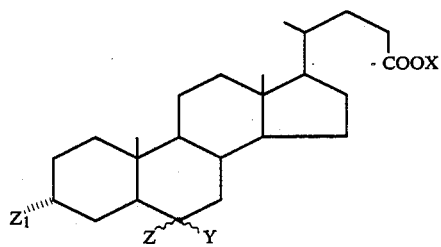

wherein Z, $Z_1$, Y and X are as defined in claim 1 and the non-toxic pharmaceutically acceptable salts thereof.

3. The Compounds of claim 1 wherein X is H; each $Z_1$ is OH; and Y is lower alkyl.

4. The Compounds of claim 1 wherein X is H; each $Z_1$ is OH; and Y is methyl.

5. 3α, 6β-Dihydroxy-6α-methyl-5β-cholanoic acid.

6. 3α, 6β-Dihydroxy-6β-methyl-5β-cholanoic acid.

7. The compounds of claim 1, herein Y is α-lower alkyl.

8. The compounds of claim 1, wherein Y is β-lower alkyl.

* * * * *